(12) United States Patent
Kouno

(10) Patent No.: US 8,723,935 B2
(45) Date of Patent: May 13, 2014

(54) IMAGE PROCESSING DEVICE, COMPUTER READABLE STORAGE MEDIUM STORING IMAGE PROCESSING PROGRAM AND IMAGE PROCESSING METHOD

(75) Inventor: Takashi Kouno, Hachioji (JP)

(73) Assignee: Olympus Corporation, Tokyo (JP)

( * ) Notice: Subject to any disclaimer, the term of this patent is extended or adjusted under 35 U.S.C. 154(b) by 114 days.

(21) Appl. No.: 12/693,059

(22) Filed: Jan. 25, 2010

(65) Prior Publication Data

US 2010/0194992 A1    Aug. 5, 2010

(30) Foreign Application Priority Data

Feb. 4, 2009  (JP) ................. 2009-024189

(51) Int. Cl.
*H04N 5/14* (2006.01)
(52) U.S. Cl.
USPC ........................ 348/65; 348/77; 348/700
(58) Field of Classification Search
CPC . H04N 5/14; H04N 2005/2255; H04N 5/147; A61B 1/041
USPC .......... 375/240.01–240.29; 348/699–701, 65, 348/77
See application file for complete search history.

(56) References Cited

U.S. PATENT DOCUMENTS

| | | | | |
|---|---|---|---|---|
| 5,635,982 | A * | 6/1997 | Zhang et al. | 348/231.99 |
| 5,995,095 | A * | 11/1999 | Ratakonda | 715/255 |
| 6,549,643 | B1 * | 4/2003 | Toklu et al. | 382/107 |
| 7,184,100 | B1 * | 2/2007 | Wilf et al. | 348/700 |
| 2006/0193387 | A1 * | 8/2006 | Wu et al. | 375/240.16 |

FOREIGN PATENT DOCUMENTS

| | | |
|---|---|---|
| JP | 08-237549 A | 9/1996 |
| JP | 2001-527304 A | 12/2001 |
| JP | 2006-41794 | 2/2006 |
| JP | 2006-334297 A | 12/2006 |
| JP | 2009-011563 A | 1/2009 |
| WO | WO 99/32993 A1 | 7/1999 |
| WO | WO 2008/041401 A1 | 4/2008 |
| WO | WO 2009/008125 A1 | 1/2009 |

OTHER PUBLICATIONS

Japanese Office Action dated Mar. 19, 2013 in Japanese Patent Application No. 2009-024189.

* cited by examiner

*Primary Examiner* — Y Lee
*Assistant Examiner* — Francis G Geroleo
(74) *Attorney, Agent, or Firm* — Scully, Scott, Murphy & Presser, P.C.

(57) ABSTRACT

An image processing device includes a change-between-images calculating unit that calculates an amount of change between images in time-series images sequentially obtained, the amount of change between images indicating an amount of change between each of the time-series images and a close image temporally close to the each of the time-series images; a primary-digest-image-group extracting unit that extracts a group of primary digest images from the time-series images on the basis of the amount of change between images; a change-in-section calculating unit that calculates an amount of change between time-series sections of the time-series images, each of the time-series sections being defined by each image of the group of primary digest images; and a digest-image-group extracting unit that extracts a group of digest images from the time-series images on the basis of both the amount of change between images and the amount of change between time-series images.

8 Claims, 13 Drawing Sheets

| IMAGE NUMBER | AMOUNT OF CHANGE BETWEEN IMAGES (-1.0 TO 1.0) |
|---|---|
| 1 | -1.00 |
| 2 | -0.33 |
| 3 | 0.85 |
| 4 | 0.66 |
| 5 | -0.58 |
| 6 | 0.86 |
| 7 | 0.86 |
| 8 | 0.84 |
| 9 | 0.83 |
| 10 | 0.83 |
| 11 | 0.81 |
| 12 | 0.79 |
| 13 | 0.77 |
| 14 | 0.76 |
| 15 | 0.76 |
| 16 | 0.75 |
| 17 | -0.14 |
| 18 | 0.65 |
| 19 | 0.22 |
| 20 | 0.81 |

FIG.6

| IMAGE NUMBER | AMOUNTS OF CHANGE BETWEEN IMAGES (-1.0 TO 1.0) AFTER SORTING |
|---|---|
| 1 | -1.00 |
| 5 | -0.58 |
| 17 | -0.14 |
| 2 | -0.33 |
| 19 | 0.22 |
| 18 | 0.65 |
| 4 | 0.66 |
| 16 | 0.75 |
| 14 | 0.76 |
| 15 | 0.76 |
| 13 | 0.77 |
| 12 | 0.79 |
| 11 | 0.81 |
| 20 | 0.81 |
| 9 | 0.83 |
| 10 | 0.83 |
| 8 | 0.84 |
| 3 | 0.85 |
| 6 | 0.86 |
| 7 | 0.86 |

| IMAGE NUMBER | PRIMARY DIGEST NUMBER | AMOUNT OF CHANGE IN SECTION (-1.0 TO 1.0) |
|---|---|---|
| 4 | 1 | 0.72 |
| 16 | 2 | 0.12 |
| 18 | 3 | 0.43 |

FIG. 13

| IMAGE NUMBER | PRIMARY DIGEST NUMBER | AMOUNTS OF CHANGE (-1.0 TO 1.0) AFTER SORTING THAT INCLUDE AMOUNTS OF CHANGE BETWEEN IMAGES OR AMOUNTS OF CHANGE IN SECTIONS | |
|---|---|---|---|
| 1 | - | -1.00 | |
| 5 | - | -0.58 | |
| 17 | - | -0.14 | |
| 2 | - | -0.33 | |
| 16 | 2 | 0.12 | ~R1 |
| 19 | - | 0.22 | |
| 18 | 3 | 0.43 | |
| 18 | - | 0.65 | |
| 4 | - | 0.66 | ~R5 |
| 4 | 1 | 0.72 | ~R7 |
| 16 | - | 0.75 | ~R3 |
| 14 | - | 0.76 | |
| 15 | - | 0.76 | |
| 13 | - | 0.77 | |
| 12 | - | 0.79 | |
| 11 | - | 0.81 | |
| 20 | - | 0.81 | |
| 9 | - | 0.83 | |
| 10 | - | 0.83 | |
| 8 | - | 0.84 | |
| 3 | - | 0.85 | |
| 6 | - | 0.86 | |
| 7 | - | 0.86 | |

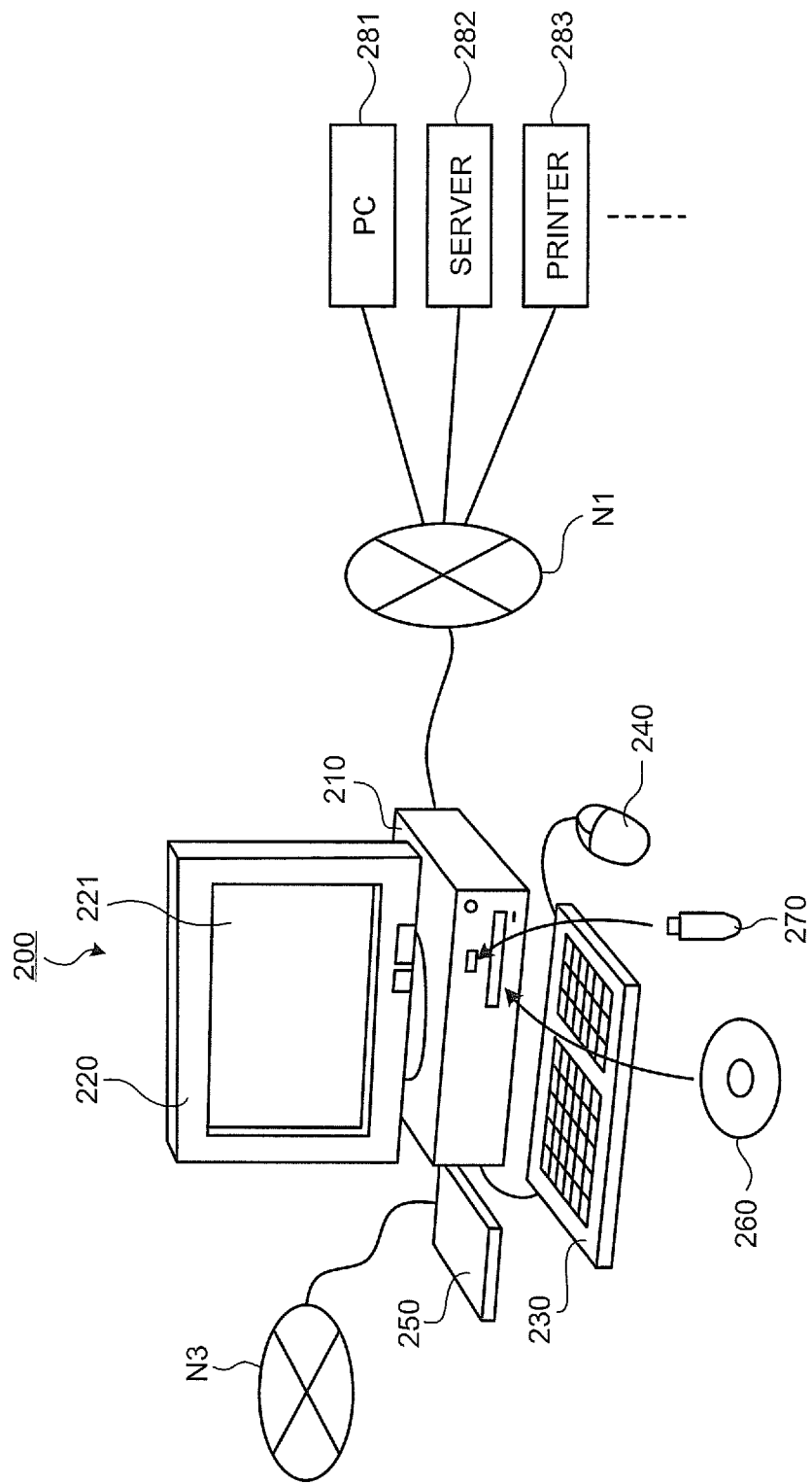

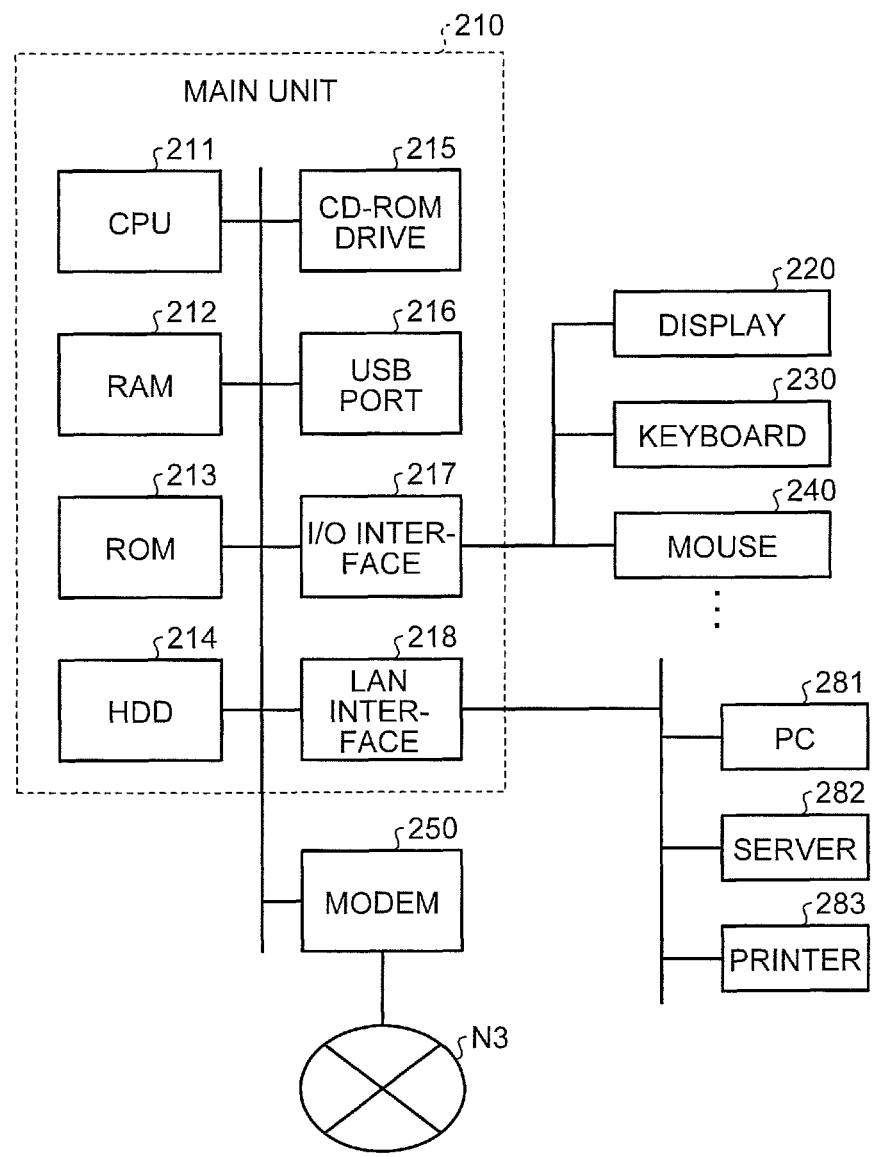

IMAGE PROCESSING DEVICE, COMPUTER READABLE STORAGE MEDIUM STORING IMAGE PROCESSING PROGRAM AND IMAGE PROCESSING METHOD

CROSS-REFERENCE TO RELATED APPLICATIONS

This application is based upon and claims the benefit of priority from Japanese Patent Application No. 2009-024189, filed on Feb. 4, 2009, the entire contents of which are incorporated herein by reference.

BACKGROUND OF THE INVENTION

1. Field of the Invention

The present invention relates to an image processing device that extracts a group of digest images from a plurality of time-series images that are taken at different points of time and arranged in chronological order, a computer readable storage medium that stores therein an image processing program, and an image processing method.

2. Description of the Related Art

A technology is known that extracts helpful images, e.g., images indicative of positions of scene changes, from time-series images, such as video images or a series of still images, as a group of digest images. A user can quickly grasp the outline of the time-series images just by scanning the extracted group of the digest images without scanning all the time-series images and, moreover, select desired scenes or images in a simple manner.

A typical, well-known manner of extracting a group of digest images involves calculating the amount of change between adjacent images and then extracting an image having a large amount of change on the basis of the calculated amount of change. For example, Japanese Patent Application Laid-open No. 2006-41797 discloses a technology that compares the amount of change between adjacent images (adjacent frames) with a predetermined threshold and extracts an image at a changing point where adjacent frames show a change that is greater than or equal to the threshold.

SUMMARY OF THE INVENTION

An image processing device according to an aspect of the present invention includes a change-between-images calculating unit that calculates an amount of change between images in time-series images that are made up of a plurality of images sequentially obtained, the amount of change between images indicating an amount of change between each of the time-series images and a close image temporally close to the each of the time-series images; a primary-digest-image-group extracting unit that extracts a group of primary digest images from the time-series images on the basis of the amount of change between images; a change-in-section calculating unit that calculates an amount of change in section with respect to a time-series image section of the time-series images, the time-series section being defined by each image of the group of primary digest images; and a digest-image-group extracting unit that extracts a group of digest images from the time-series images on the basis of both the amount of change between images and the amount of change in section.

A computer readable recording medium according to another aspect of the present invention has stored therein an image processing program including instructions. The instructions cause a computer to execute calculating an amount of change between images in time-series images that are made up of a plurality of images sequentially obtained, the amount of change between images indicating an amount of change between each of the time-series images and a close image temporally close to the each of the time-series images; extracting a group of primary digest images from the time-series images on the basis of the amount of change between images; calculating an amount of change in section with respect to a time-series image section of the time-series images, the time-series section being defined by each image of the group of primary digest images; and extracting a group of digest images from the time-series images on the basis of both the amount of change between images and the amount of change between time-series images.

An image processing method according to still another aspect of the present invention includes calculating an amount of change between images in time-series images that are made up of a plurality of images sequentially obtained, the amount of change between images indicating an amount of change between each of the time-series images and a close image temporally close to the each of the time-series images; extracting a group of primary digest images from the time-series images on the basis of the amount of change between images; calculating an amount of change in section with respect to a time-series image section of the time-series images, the time-series section being defined by each image of the group of primary digest images; and extracting a group of digest images from the time-series images on the basis of both the amount of change between images and the amount of change between time-series images.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 6 is a table of the amounts of change between the images, which are contained in the table shown in FIG. 4, after sorting;

FIG. 13 is a table of amounts of change after sorting that includes both the amounts of change between the images shown in FIG. 4 or 6 and the amounts of change in sections shown in FIG. 11;

FIG. 16 is a schematic diagram of the configuration of a computer system used in the embodiments; and FIG. 17 is a block diagram of a main unit included in the computer system shown in FIG. 16.

DETAILED DESCRIPTION OF THE PREFERRED EMBODIMENTS

Figure 1:
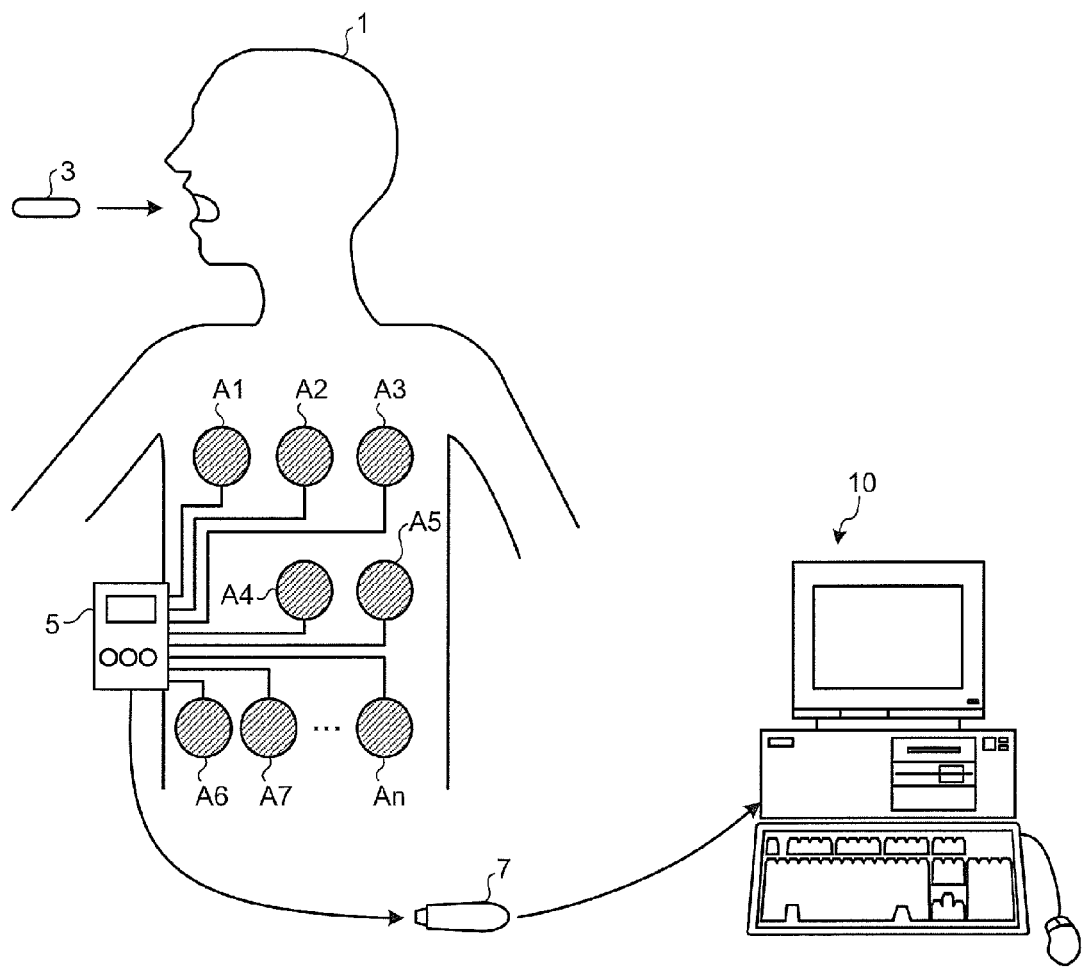
FIG. 1 is a schematic diagram of an image processing system that includes an image processing device.

Exemplary embodiments of the present invention are described in detail below with reference to the accompanying drawings. In the following embodiments, image processing devices are used that process time-series images of an inner body cavity, such as an alimentary track, taken by a capsule endoscope moving inside the body cavity. It is noted that the present invention is not limited to the following embodiments. In the drawings, the same parts are denoted with the same reference numerals.

A first embodiment of the present invention is described below. FIG. 1 is a schematic diagram of an image processing system that includes an image processing device according to a first embodiment of the present invention. As shown in FIG. 1, the image processing system includes a capsule endoscope 3, a receiving device 5, an image processing device 10, etc. The capsule endoscope 3 takes images of an inner part of a subject 1. The receiving device 5 receives the images wirelessly from the capsule endoscope 3. The image processing device 10 processes the images taken by the capsule endoscope 3 using the images received by the receiving device 5 and displays the processed images. To transfer image data between the receiving device 5 and the image processing device 10, for example, a recording medium that can be carried (potable recording medium) 7 is used.

The capsule endoscope 3 has an imaging function and a wireless communication function, etc. After swallowed through the mouth of the subject 1 and introduced inside the subject 1, the capsule endoscope 3 sequentially takes images, while moving inside the body cavity. The capsule endoscope 3 then wirelessly sends the taken images outside the body. The images taken by the capsule endoscope 3 includes, for example, mucosa membranes, content pieces that are floating inside the body cavity, and bubbles. Some images include an important part such as lesions. The total number of the images taken by the capsule endoscope 3 is roughly represented by imaging rate(about 2 to 4 frames/sec)×time of the capsule endoscope being in the body(about 8 hours=8×60×60 sec), i.e., several tens of thousands frames or more are taken in total. The inner-body-cavity images taken by the capsule endoscope 3 are color images including pixels each having a pixel value corresponding to each of the wavelength components red (R), green (G), blue (B).

The receiving device 5 includes a plurality of receiving antennas A1 to An arranged at different points on the body surface along the passage of the capsule endoscope 3 moving inside the subject 1. The receiving device 5 receives image data wirelessly from the capsule endoscope 3 via the receiving antennas A1 to An. The receiving device 5 is configure to attach to or detach from the potable recording medium 7 and sequentially stores the received image data in the potable recording medium 7. In this manner, the images of the inner parts of the subject 1 taken by the capsule endoscope 3 are stored in the potable recording medium 7 arranged in chronological order as the time-series images.

The image processing device 10 allows a doctor or the like to check the images taken by the capsule endoscope 3 for observation or diagnosis. The image processing device 10 is implemented by a general-purpose computer, such as a workstation or a personal computer. The image processing device 10 is configured to attach to or detach from the potable recording medium 7. The image processing device 10 processes the time-series images stored in the potable recording medium 7 and displays, if required, the processed images on a display, such as an LCD and an EL display.

Figure 2:
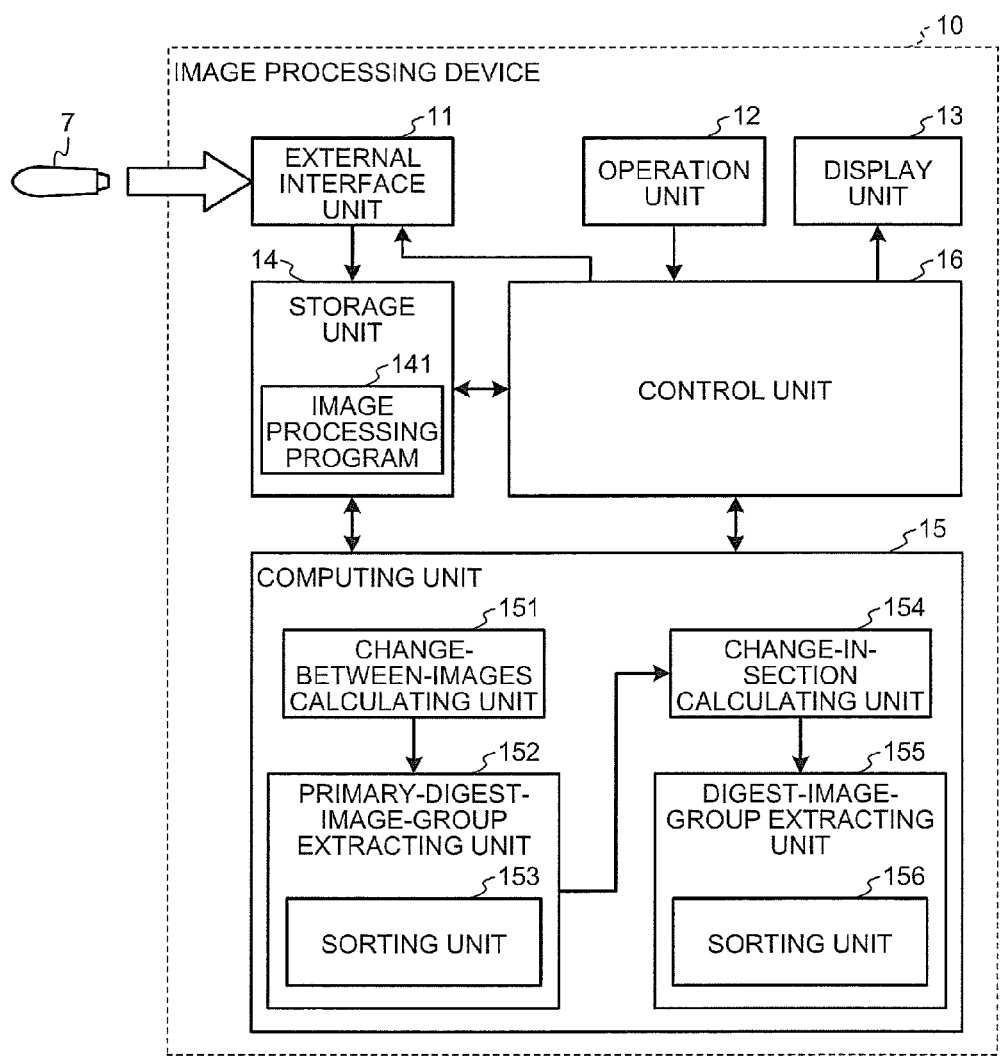
FIG. 2 is a block diagram of the functional configuration of the image processing device according to the first embodiment.

FIG. 2 is a block diagram of the functional configuration of the image processing device 10 according to the first embodiment. The image processing device 10 according to the first embodiment includes an external interface unit 11, an operation unit 12, a display unit 13, a storage unit 14, a computing unit 15, and a control unit 16 that controls the operation of the image processing device 10.

The external interface unit 11 obtains the image data that has been taken by the capsule endoscope 3 and received by the receiving device 5. The external interface unit 11 is, for example, a reading device that is configured to attach to and detach from the potable recording medium 7 and reads data containing the time-series images from the potable recording medium 7. When the image data is read from the potable recording medium 7 via the external interface unit 11, the image data is stored in the storage unit 14. The computing unit 15 processes the image data stored in the storage unit 14, and the display unit 13 displays the processed image data under the control of the control unit 16. Although the image processing device 10 obtains the image data taken by the capsule endoscope 3 via the potable recording medium 7, the configuration is not limited thereto. For example, the data containing the time-series images taken by the capsule endoscope 3 can be stored in a server instead of the potable recording medium 7. In this case, the external interface unit 11 is configured as a communication device or the like that connects the image processing device to the server. The image processing device makes data communications with the server via the external interface unit 11 and obtains the image data from the server. Alternatively, it is allowable to store the data containing the time-series images taken by the capsule endoscope 3 directly in the storage unit 14 and obtain the image data from the storage unit 14.

The operation unit 12 is implemented by, for example, a keyboard, a mouse, a touch panel, various switches, etc. The operation unit 12 outputs an operation signal to the control unit 16. The display unit 13 is a display device, such as an LCD or an EL display. The display unit 13 displays various screens under the control of the control unit 16, such as a screen with the images taken by the capsule endoscope 3.

The storage unit 14 is implemented by an information storage medium, a reading device that reads the information storage medium, etc. The information recording medium is, for example, various IC memories, such as a ROM or a RAM that is an updatable flash memory, a built-in hard disk, an external hard disk that is connected to the image processing device 10 via a data communication terminal, and a CD-ROM. The storage unit 14 stores therein computer programs that activate the image processing device 10 and implements various functions of the image processing device 10 and data that is used in the computer programs. The storage unit 14 stores therein, for example, the data containing the time-series images, which has been obtained via the external interface unit 11, and their image numbers in an associated manner. The image number is used to identify the chronological order position of the corresponding image. The storage unit 14 stores therein an image processing program 141 that is used to extract a group of digest images from the time-series images.

The computing unit 15 processes the time-series images taken by the capsule endoscope 3 and performs various computing processes to extract a group of digest images. The computing unit 15 includes a change-between-images calculating unit 151, a primary-digest-image-group extracting unit 152, a change-in-section calculating unit 154, and a digest-image-group extracting unit 155. The change-between-images calculating unit 151 calculates the amount of change between images selected from the time-series images (hereinafter, "amount of change between images"). The primary-digest-image-group extracting unit 152 extracts, using the magnitude of change indicated by the amount of change between the images, an image to be included in a group of primary digest images from the time-series images. The primary-digest-image-group extracting unit 152 includes a sorting unit 153 that sorts the amounts of change between the images by the magnitude of change. The sorting unit 153 corresponds to a second sorting unit. The change-in-section calculating unit 154 calculates the amount of change in a section of the time-series images defined by the primary digest images (hereinafter, "amount of change in a section"). The digest-image-group extracting unit 155 extracts, using the magnitude of change indicated by both the amount of change between the images and the amount of change in section, an image to be included in a group of digest images from the time-series images. The digest-image-group extracting unit 155 includes a sorting unit 156 that sorts the amounts of change in sections by the magnitude of change. The sorting unit 156 corresponds to a first sorting unit.

The control unit 16 is implemented by a hardware component, such as a CPU. The control unit 16 controls operations of the image processing device 10 by sending instructions and data to the units of the image processing device 10 in accordance with the image data that has been obtained via the external interface unit 11, the operation signal received from the operation unit 12, the computer programs and data stored in the storage unit 14, etc.

Figure 3:
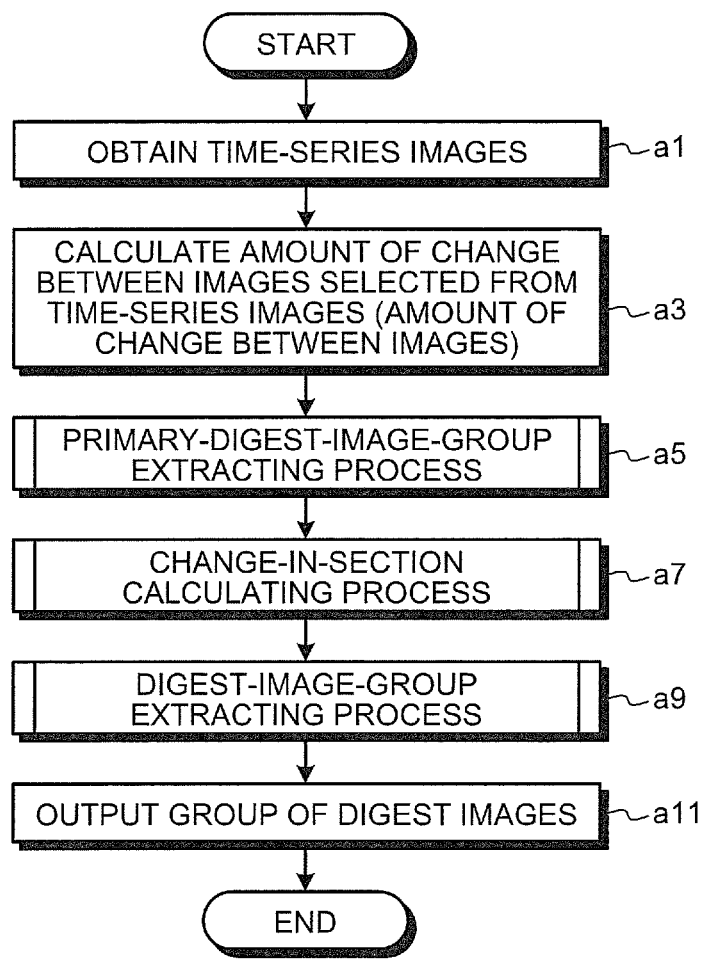
FIG. 3 is a general flowchart of a process performed by the image processing device according to the first embodiment.

FIG. 3 is a general flowchart of a process performed by the image processing device 10 according to the first embodiment. The process described with reference to FIG. 3 is implemented when the computing unit 15 performs the image processing program 141 stored in the storage unit 14.

As shown in FIG. 3, the computing unit 15 obtains time-series images in a target range (Step a1). More particularly, the computing unit 15 reads the time-series images in the target range that have been read from the potable recording medium 7 via the external interface unit 11 and stored in the storage unit 14 and obtains the read time-series images. The target range can be a sectional range of the time-series images or the complete range from the top frame to the last frame of the time-series images. The target range may be set by, for example, a user operation.

After that, the change-between-images calculating unit 151 calculates an amount of change between images selected from the time-series images (amount of change between images) (Step a3). Amount of change between images is, herein, a value indicative of change between close images temporally close to each other and calculated using, for example, a correlation value (degree of similarity). More particularly, the change-between-images calculating unit 151 selects sets the time-series images obtained at Step a1 one by one as a focus image and calculates a correlation value between the focus image and the close image as the amount of change between the images for the focus image. The close image is for example an image immediately before the focus image in chronological order.

It is possible to calculate the correlation value free from linear change in the brightness (linear change in the luminance value and the contrast) using, for example, a well-known normalized cross-correlation (NCC) (see "Normalized cross-correlation" on page 204 of "Digital image processing" by Computer Graphic Art Society). More particularly, the NCC between image data I and image data T is calculated using Equation (1):

$$R_{NCC} = \frac{\sum_{y=0}^{N-1}\sum_{x=0}^{M-1}((I(x,y)-\bar{I})(T(x,y)-\bar{T}))}{\sqrt{\sum_{y=0}^{N-1}\sum_{x=0}^{M-1}(I(x,y)-\bar{I})^2}\sqrt{\sum_{y=0}^{N-1}\sum_{x=0}^{M-1}(T(x,y)-\bar{T})^2}} \quad (1)$$

in which $\bar{I} = \frac{1}{MN}\sum_{y=0}^{N-1}\sum_{x=0}^{M-1}I(x,y)$ and $\bar{T} = \frac{1}{MN}\sum_{y=0}^{N-1}\sum_{x=0}^{M-1}T(x,y)$.

Figures 4, 5:
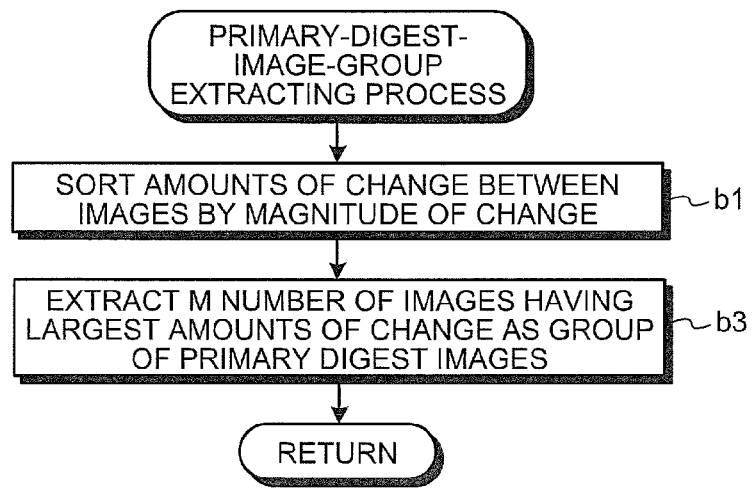
FIG. 4 is a table of amounts of change between images selected from time-series images.
FIG. 5 is a detailed flowchart of a primary-digest-image-group extracting process.

The NCC-based correlation value takes any value from −1.00 to 1.00. As the correlation value comes closer to −1.00, the magnitude of change increases. As the correlation value comes closer to 1.00, the magnitude of change decreases. The amount of change between the images associated with the top image is set to a predetermined fixed value (e.g., −1.00) because there is no image ahead thereof in chronological order. FIG. 4 is a table of the amounts of change between the images selected from the time-series images that are made up of 20 images and the image numbers allocated to the images. Data containing the calculated amount of change between the images associated with each image is stored in the storage unit 14 in associated with the image number as shown in FIG. 4.

Although the method of calculating the NCC-based correlation value as the value indicative of change between the images is described in the above example, the configuration is not limited thereto. For example, if images are not significantly affected by change in the brightness, a degree of dissimilarity, in which 0 indicates that the images are identical to each other and the value increases as the degree of the dissimilarity between the images increases, can be used. Degree of dissimilarity can be calculated using, for example, sum of squared differences (SSD) and sum of absolute differences (SAD) (see "Degree of similarity" on page 203 of "Digital image processing" by Computer Graphic Art Society).

As shown in FIG. 3, the primary-digest-image-group extracting unit 152 performs a primary-digest-image-group extracting process, i.e., extracts a group of primary digest images from the time-series images using the amounts of change between the images (Step a5). FIG. 5 is a detailed flowchart of the primary-digest-image-group extracting process.

During the primary-digest-image-group extracting process, the sorting unit 153 of the primary-digest-image-group extracting unit 152 sorts the amounts of change between the images that are calculated at Step a3 of FIG. 3 by the magnitude of change (Step b1). FIG. 6 is a table of the amounts of change between the images, which are contained in the table shown in FIG. 4, after sorting. As described above, the amounts of change between the images are calculated in the first embodiment as the NCC-based correlation values from −1.00 to 1.00. As the value comes closer to −1.00, the magnitude of change increases. This is why, in the sorting process, the amounts of change between the images are sorted in the ascending order as shown in FIG. 6.

As shown in FIG. 5, the primary-digest-image-group extracting unit 152 extracts, as a group of primary digest images, M number of images that have the largest magnitudes of change on the basis of the amounts of change between the images after sorting, (Step b3). The value of M is a predetermined value. If M is five, then, in the example shown in FIG. 6, the five images having the image numbers 1, 5, 17, 2, and 19 are extracted as a group of primary digest images. The primary-digest-image-group extracting unit 152 allocates a primary digest number to each of the extracted images. More particularly, the primary-digest-image-group extracting unit 152 allocates serial numbers to the extracted images in such a manner that an image having a smaller image number is allocated a smaller primary digest number. The value of M, which indicates the total number of the primary digest images to be extracted, can be set as a fixed value or can be set depending on the total number of time-series images. Alternatively, the value of M can be set as a variable value specified in accordance with an external input, for example, an instruction by a user. After the group of the primary digest images is extracted, the process control returns to Step a5 of FIG. 3 and then goes to Step a7.

At Step a7, the change-in-section calculating unit 154 performs a change-in-section calculating process, i.e., calculates an amount of change in each section of the time-series images defined by the primary digest images.

During the change-in-section calculating process, the change-in-section calculating unit 154 selects the primary digest images one by one as a focus primary digest image. The change-in-section calculating unit 154 then calculates the difference between the primary digest image of which the primary digest image number is one smaller than that of the focus primary digest image (hereinafter, "preceding primary digest image") and the image of which the image number is one smaller than that of the focus primary digest image, i.e., the image one image earlier in chronological order (hereinafter, "late-section image"), as the amount of change in section of the time-series images defined by both the preceding primary digest image and the focus primary digest image.

Figure 7:
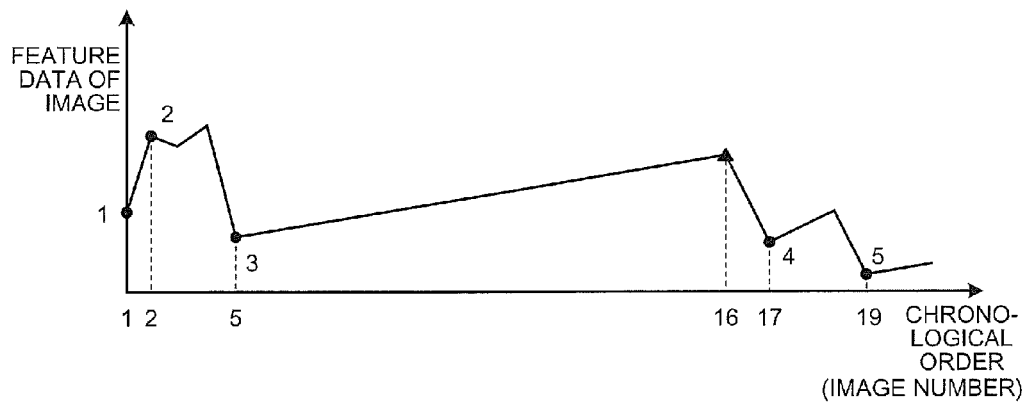
FIG. 7 is a graph that explains the principle based on which the amounts of change between the images are calculated.
Figure 8:
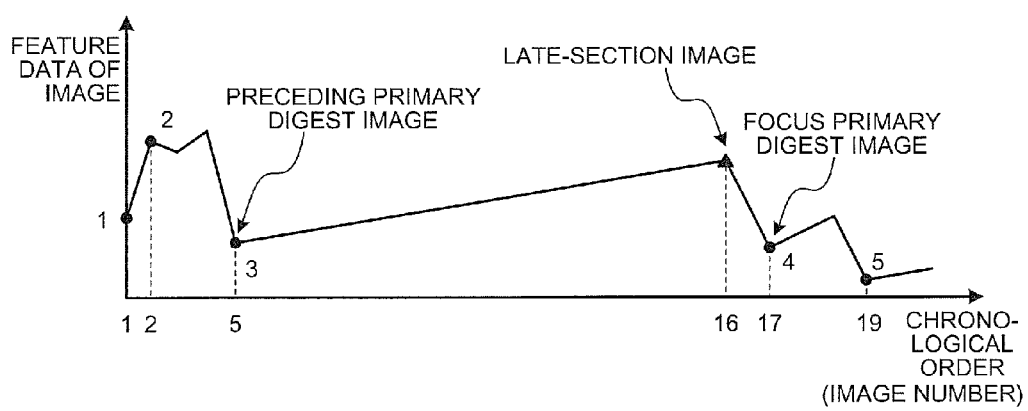
FIG. 8 is a graph that explains the principle based on which the amounts of change between the images are calculated.
Figure 9:
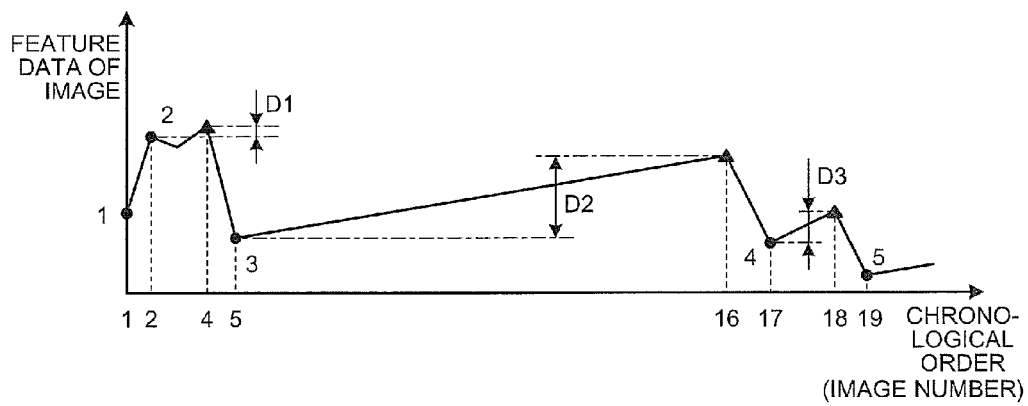
FIG. 9 is a graph that explains the principle based on which the amounts of change between the images are calculated.

The principle of calculating an amount of change in a section is described below with reference to FIGS. 7 to 9. FIGS. 7 to 9 are a graph of change over the time-series images, in which the horizontal axis is the sequence of the time-series images shown in FIGS. 4 and 6 (the image number) and the vertical axis is the feature data of the image (e.g., average luminance). The images having the image numbers 1, 5, 17, 2, and 19 that are extracted as the group of the primary digest images in accordance with the result of the sorting as shown in FIG. 6 are shown in FIGS. 7 to 9 denoted with the primary digest numbers 1, 2, 3, 4, and 5. The graph shown in FIGS. 7 to 9 indicates change over the time-series images using the average luminance of each image as the feature data. As the slope of the graph gets steeper, the magnitude of change between the images increases (i.e., in the first embodiment, the calculated value comes closer to −1.0).

As described above, the group of primary digest images is made up of M number of (five, in the example) images that have the largest magnitudes of change extracted on the basis of the calculated magnitudes of change between the target image and the image immediately before it in chronological order (i.e., the amounts of change between the images). As shown in FIG. 7, each of the images having the image numbers 1, 5, 17, 2, and 19, which make up the group of the primary digest images, is significantly different from the image immediately before. It is assumed that, for example, the section defined by the images having the image numbers 5 and 17 is in focus. The section includes the images having the image numbers 5 to 16 and the graph changes gradually in the section. The graph then changes drastically from the image having the image number 16 to the last image having the image number 17. Because of the large magnitude of change between these images, the image having the image number 17 is extracted as a primary digest image.

Although individual changes between images in a section are small, the magnitude of change in a section can be large due to accumulation of the small changes. In the focused section from the image number 5 to the image number 16, although the magnitudes of change between images that are temporally close to each other (more specifically, adjacent images in the example) are small, the difference between the images having the image numbers 5 and 16 is significantly large, i.e., the magnitude of change in section is large. To select a group of digest images with a large magnitude of change in a section being taken into consideration, the magnitude of change in each section defined by the primary digest images is calculated as the amount of change in each section.

For example, as shown in FIG. 8, if the image having the primary digest number 4 and the image number 17 is the focus primary digest image, the image having the primary digest number 3 and the image number 5 is set to the preceding primary digest image. Accordingly, the image having the image number 16 is set to the late-section image. A difference between the preceding primary digest image and the late-section image is calculated as the amount of change in section (ranging from the preceding primary digest image to the focus primary digest image).

As shown in FIG. 9, when the image having the primary digest number 3 and the image number 5 is selected as the focus primary digest image, a difference D1 between the preceding primary digest image (i.e., the image having the primary digest number 2 and the image number 2) and the late-section image (i.e., the image having the image number 4) is calculated as the amount of change in section. When the image having the primary digest number 4 and the image number 17 is selected as the focus primary digest image, a difference D2 between the preceding primary digest image (i.e., the image having the primary digest image 3 and the image number 5) and the late-section image (i.e., the image having the image number 16) is calculated as the amount of change in section. When the image having the primary digest number 5 and the image number 19 is selected as the focus primary digest image, a difference D3 between the preceding primary digest image (i.e., the image having the primary digest image 4 and the image number 17) and the late-section image (i.e., the image having the image number 18) is calculated as the amount of change in section. It is noted that the amount of change in section is calculated only if the chronological order position (the image number) of the late-section image is subsequent to the chronological order position (the image number) of the preceding primary digest image. In other words, when the image having the primary digest number 2 and the image number 2 is selected as the focus primary digest image, the amount of change in section is not calculated because the image of which the primary digest number is one smaller (i.e., the image having the primary digest image 1 and the image number 1) is identical to the image of which the chronological order position (the image number) is one smaller (i.e., the image having the image number 1).

Figure 10:
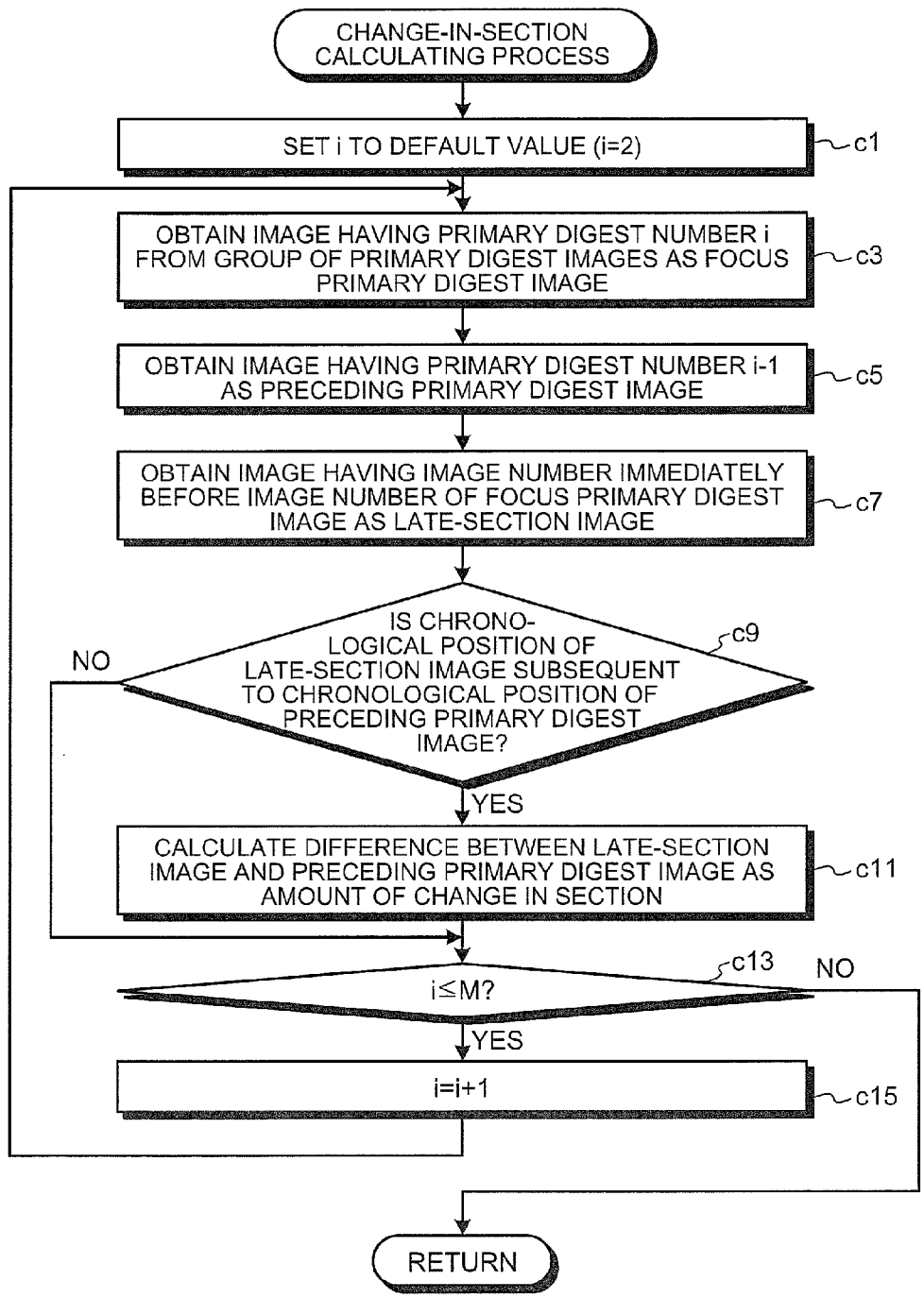
FIG. 10 is a detailed flowchart of a change-in-section calculating process.

FIG. 10 is a detailed flowchart of the change-in-section calculating process. During the change-in-section calculating process, under an actual situation, the change-in-section calculating unit 154 sets a parameter i indicative of the focus primary digest image to a default value (Step c1). To set the image having the primary digest number 2 as the focus primary digest image at the start of the process, the default value of i is two. This is because there is no preceding primary digest image of the image having the primary digest number 1. The change-in-section calculating unit 154 then obtains the image having the primary digest number i as the focus primary digest image (Step c3).

After that, the change-in-section calculating unit 154 obtains the image having the primary digest number i-1, which is the image having the primary digest number immediately before the primary digest number of the focus primary digest image, from the group of the primary digest images as the preceding primary digest image (Step c5). The change-in-section calculating unit 154 obtains, as the late-section image, the image of which the image number is one smaller than the image number of the focus primary digest image (Step c7).

After that, the change-in-section calculating unit 154 determines whether the chronological order position (the image number) of the late-section image is subsequent to the chronological order position (the image number) of the preceding primary digest image. If the determination is positive (Yes at Step c9), the process control goes to Step c11. More particularly, the change-in-section calculating unit 154 calculates a difference between the preceding primary digest image and the late-section image as the amount of change in section at Step c11.

Amount of change in section is a value indicative of change in section defined by the primary digest images and, more particularly, corresponds to a difference between the preceding primary digest image and the late-section image. An NCC-based correlation value (degree of similarity) between the images can be used as the amount of change in section in the same manner as in the amount of change between the images. Alternatively, some other values, such as degree of dissimilarity, can be used.

After that, the change-in-section calculating unit 154 determines whether the primary digest number i is equal to or smaller than M, i.e., determines whether the focus primary digest image is the last image of the primary digest images. If i is equal to or smaller than M, i.e., the focus primary digest image is not the last image (Yes at Step c13), the parameter i is incremented (Step c15) and the change-in-section calculating unit 154 performs the processes of Steps c3 to c13 with the next focus primary digest image. If it is determined the last image of the primary digest images has been subjected to the process (No at Step c13), the process control returns to Step a7 of FIG. 3 and then goes to Step a9.

Figures 11, 12:
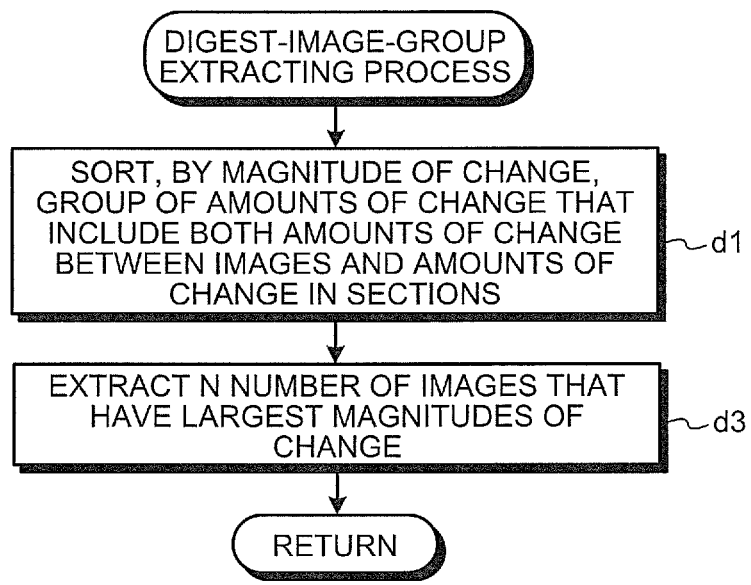
FIG. 11 is a table of amounts of change in sections defined by primary digest images that are extracted in accordance with the result of the sorting shown in FIG. 6.
FIG. 12 is a detailed flowchart of a digest-image-group extracting process.

FIG. 11 is a table of the amounts of change in sections defined by the images having the image numbers 1, 5, 17, 2, and 19 that are extracted as the group of the primary digest images in accordance with the result of the sorting shown in FIG. 6. The table includes the primary digest image numbers and the image numbers of the late-section images. Data containing the calculated amount of change in each section is stored in the storage unit 14 in associated with at least the image number of the late-section image. In the subsequent processes, it is assumed that the calculated amount of change in each section is associated with the late-section image.

Although, in the above-described example, the image immediately before the focus primary digest image is obtained as the late-section image, the late-section image is not limited thereto. More particularly, it is possible to obtain an image n frame(s) before the focus primary digest image in chronological order as the late-section image. The value of n can be set as a fixed value or a variable value specified in accordance with an external input, for example, an instruction by a user.

As shown in FIG. 3, at Step a9, the digest-image-group extracting unit 155 performs a digest-image-group extracting process, i.e., extracts a group of digest images from the time-series images using both the amounts of change between the images and the amounts of change in sections. FIG. 12 is a detailed flowchart of the digest-image-group extracting process.

During the digest-image-group extracting process, the sorting unit 156 of the digest-image-group extracting unit 155 sorts a group of amounts of change that include both the amounts of change between the images calculated at Step a3 of FIG. 3 and the amounts of change in sections associated with the late-section images calculated at Step a7 by the magnitude (Step d1). FIG. 13 is a table of the amounts of change after sorting that includes both the amounts of change between the images shown in FIG. 4 or 6 and the amounts of change in sections shown in FIG. 11.

In the above example, the amounts of change that include both the amounts of change between the images and the amounts of change in sections are sorted by the magnitude. However, if N indicative of the number of images to be extracted at the subsequent Step d3 as a group of digest images is equal to or smaller than M indicative of the number of the primary digest images, it is allowable to sort the amounts of change that include only the amounts of change between the images associated with the primary digest images (i.e., in the above-described example with reference to FIG. 6, the amounts of change between the images associated with the images having the image numbers 1, 5, 17, 2, and 19) and the amounts of change in sections associated with the late-section images having the image numbers 4, 16, and 18. This is because it is unnecessary to sort the images unextracted as the group of the primary digest images due to their small magnitudes of change. This reduces the amount of the data to be subjected to the sorting process, which shortens the processing time.

As shown in FIG. 12, the digest-image-group extracting unit 155 extracts, as a group of digest images, N number of images that have the largest magnitudes of change on the basis of the amounts of change after sorting that include both the amounts of change between the images and the amounts of change in sections (Step d3). It is assumed that N is, for example, five. In this case, as described above with reference to FIG. 6, although the images having the image numbers 1, 5, 17, 2, and 19 are extracted as the group of the primary digest images, the images having the image numbers 1, 5, 17, 2, and 16 are extracted as the group of the digest images. This is because the calculated amount of change in section associated with the late-section image having the image number 16 (i.e., the difference between the two images having the image numbers 5 and 16) is larger than the calculated amount of change between the images associated with the image having the image number 19 (i.e., the magnitude of change between the two images having the image numbers 18 and 19).

Because, in this example, the amount of change in section is assigned to the late-section image, the late-section image has two amounts of change, i.e., the amount of change between the images and the amount of change in section. For example, the image having the image number 16 has a record R1 indicative of the amount of change between the images and a record R3 indicative of the amount of change in section. If the group of the digest images in total N frames includes amounts of change assigned to the same image number, the record having the larger magnitude of change is taken. If, for example, N=10 and a group of ten digest images is to be extracted in accordance with the result of the sorting shown in FIG. 13, each of the images having the image numbers 4 and 16 has overlapped records in the list. Because a record having the larger magnitude of change is to be taken, the amount of change between the images indicated by a record R5 is taken as the amount of change associated with the image number 4 and the amount of change in section indicated by a record R1 is taken as the amount of change associated with the image number 16. As a result, the top ten records, except for the amount of change in section associated with the image number 4 (record R7) and the amount of change between the images associated with the image number 16 (record R3) are extracted as a group of digest images, in accordance with the result of the sorting.

The value of N, which indicates the number of images to be extracted as a group of digest images, can be set as a fixed value or can be set depending on the total number of time-series images. Alternatively, the value of N can be set as a variable value specified in accordance with an external input, for example, an instruction by a user. After the group of the digest images is extracted, the process control returns to Step a9 of FIG. 3 and then goes to Step a11.

At Step a11, the computing unit 15 outputs the group of the digest images. For example, the computing unit 15 causes the display unit 13 to display the images that are extracted as the group of the digest images one by one. The process performed by the computing unit 15 of the image processing device 10 is thus completed.

As described above, in the first embodiment, the magnitude of change between adjacent images selected from time-series images (amount of change between images) is calculated and a group of primary digest images is extracted using the calculated amounts of change between the images. After that, the amount of change in each section of the time-series images defined by the primary digest images is calculated. A group of digest images is extracted using both the amounts of change between the images and the amounts of change in sections. With this configuration, because a large change in a section due to accumulation of small changes between the images is taken into consideration, appropriate digest images are extracted. As an example of the first embodiment, a group of appropriate digest images is extracted from many frames of the time-series images taken by the capsule endoscope 3, which allows an observer, such as a doctor, to check the time-series images with a higher efficiency.

More particularly, the primary digest images are selected one by one as the focus primary digest image. A difference between the preceding primary digest image that is the primary digest image immediately before the focus primary digest image in chronological order and the late-section image that is the image immediately before the focus primary digest image in chronological order is calculated as the amount in the section. Therefore, a late-section image having a large amount of change in section is extracted as a digest image. Accordingly, if there is a section in which although the individual changes between the images are small, the late-section image is significantly different from the top image, i.e., the magnitude of change in section is large, the late-section image of the section is extracted as a digest image.

The amount of change in each section of the time-series images defined by the primary digest images that are extracted using the amounts of change between the images is calculated only by calculating the difference between the preceding primary digest image of the focus primary digest image and the late-section image of the focus primary digest image. In this manner, the amount of change in each section is calculated in the simple manner and therefore the processing load is reduced.

Figure 14:
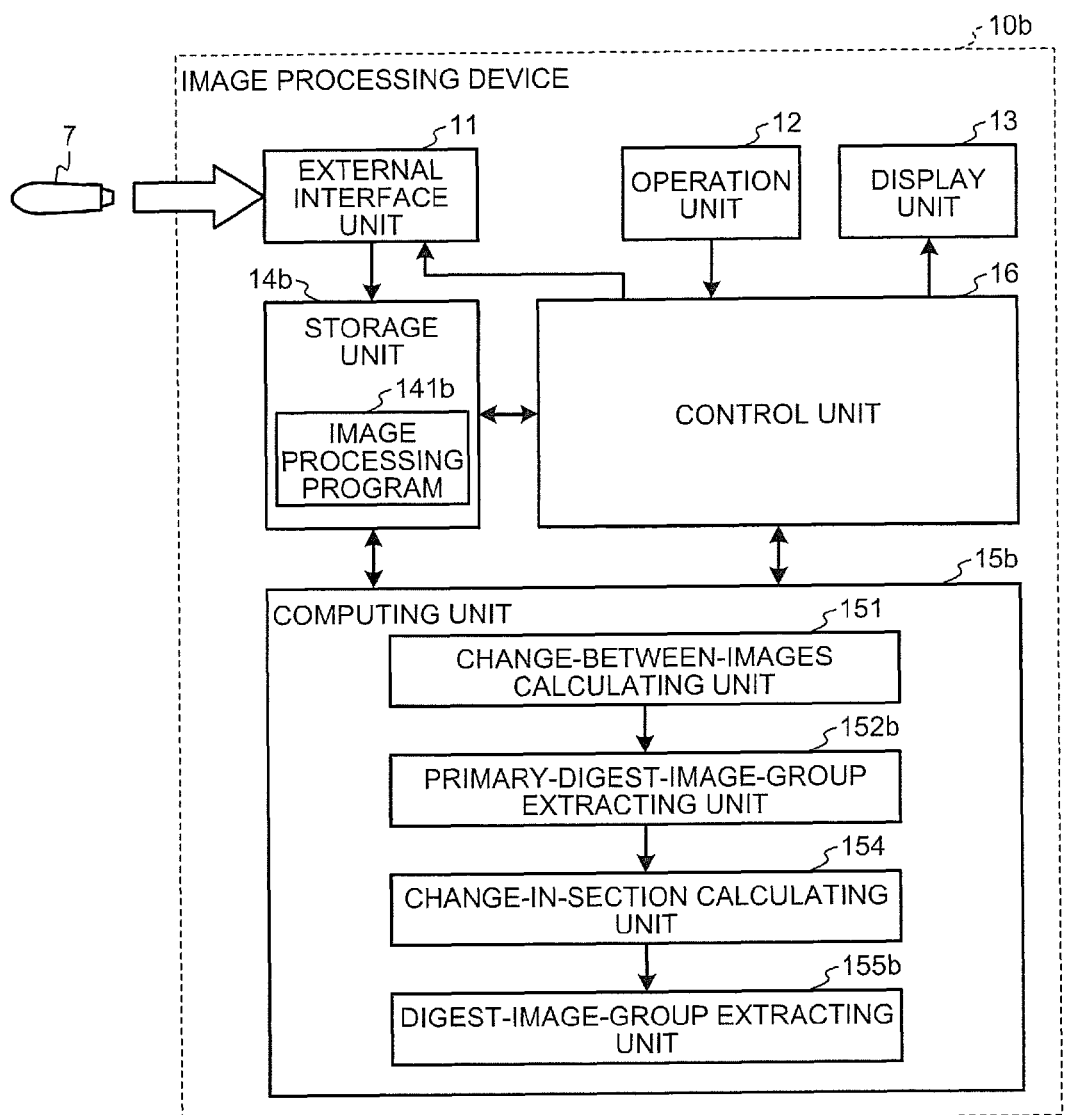
FIG. 14 is a block diagram of the functional configuration of an image processing device according to the second embodiment.

A second embodiment of the present invention is described below. FIG. 14 is a block diagram of the functional configuration of an image processing device 10*b* according to the second embodiment. Parts corresponding to those described in the first embodiment are denoted with the same reference numerals. As shown in FIG. 14, the image processing device 10*b* includes the external interface unit 11, the operation unit 12, the display unit 13, a storage unit 14*b*, a computing unit 15*b*, and the control unit 16 that controls the operation of the image processing device 10*b*.

The storage unit 14*b* stores therein an image processing program 141*b* that is used to extract a group of digest images from the time-series images.

The computing unit 15*b* includes the change-between-images calculating unit 151, a primary-digest-image-group extracting unit 152*b*, the change-in-section calculating unit 154, and a digest-image-group extracting unit 155*b*. In the second embodiment, the primary-digest-image-group extracting unit 152*b* extracts a group of primary digest images by comparing the amount of change between the images with a threshold. The digest-image-group extracting unit 155*b* extracts a group of digest images by comparing with a threshold each of the amount of change between the images and the amount of change in section.

The difference between the image processing device 10*b* according to the second embodiment different and the image processing device 10 according to the first embodiment is that both the primary-digest-image-group extracting unit 152*b* and the digest-image-group extracting unit 155*b* include no sorting units.

Figure 15:
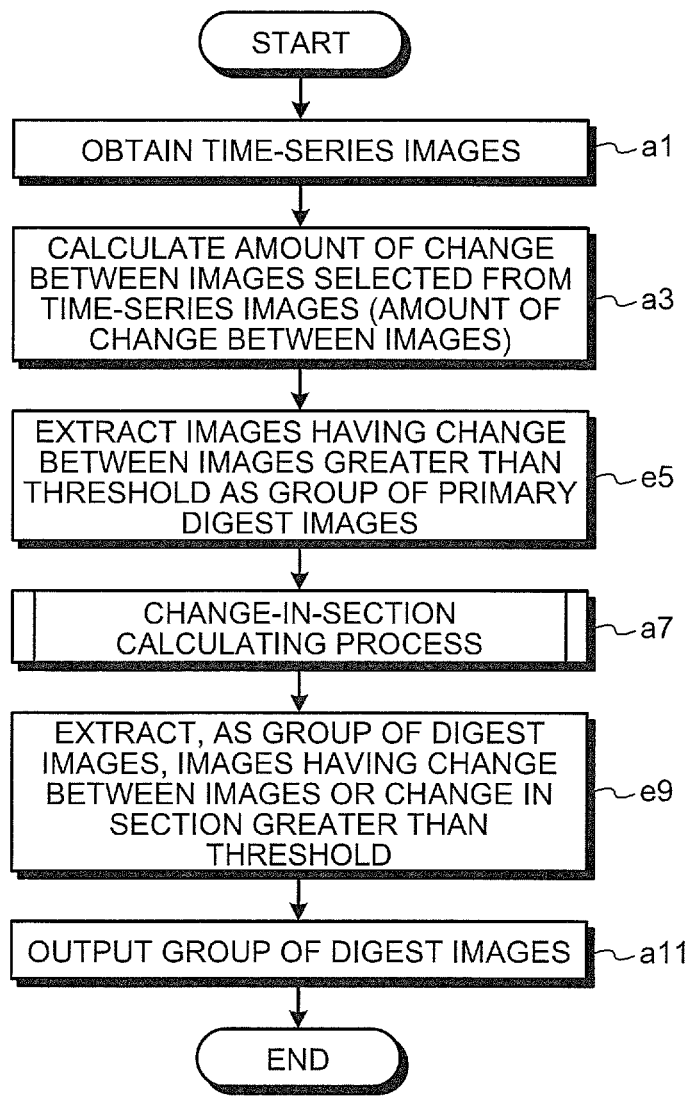
FIG. 15 is a general flowchart of a process performed by the image processing device according to the second embodiment.

FIG. 15 is a general flowchart of a process performed by the image processing device 10*b* according to the second embodiment. The process described with reference to FIG. 15 is implemented when the computing unit 15*b* performs the image processing program 141*b* stored in the storage unit 14*b*. Steps the same as those in the first embodiments are denoted with the same reference numerals.

In the second embodiment, as shown in FIG. 15, after the change-between-images calculating unit 151 calculates the amount of change between the images at Step a3, the primary-digest-image-group extracting unit 152*b* compares the amount of change between the images with a threshold and extracts an image having change between the images greater than the threshold as a primary digest image (Step e5). The threshold used at Step e5 can be set as a fixed value or a variable value specified in accordance with an external input, for example, an instruction by a user.

After that, the change-in-section calculating unit 154 performs the change-in-section calculating process (see FIG. 10) in the same manner as in the first embodiment, thereby calculating the amount of change in each section of the time-series images defined by the primary digest images (Step a7).

The digest-image-group extracting unit 155*b* compares with a threshold each of the amount of change between the images and the amount of change in section associated with the late-section image and extracts an image having change between the images or change in section greater than the threshold as a digest image (Step e9). The threshold used at Step e9 can be equal to or different from the threshold used at Step e5. The threshold used at Step e9 can be set as a fixed value or a variable value specified in accordance with an external input, for example, an instruction by a user.

After that, the computing unit 15b outputs the group of the digest images (Step a11) and the process performed by the computing unit 15b of the image processing device 10b is completed.

As described above, in the second embodiment, the group of primary digest images is extracted by comparing the amount of change between the images with the threshold; and the group of digest images is extracted by comparing with the threshold each of the amount of change between the images and the amount of change in section. In this manner, the same effects obtained in the first embodiment are obtained in the second embodiment. Moreover, the processing load necessary for the processes using the thresholds according to the second embodiment is smaller than the processing load necessary for the sorting processes according to the first embodiment, which brings the effect of reducing the processing load.

Although, in the above-described embodiments, a group of digest images is extracted from the time-series images taken by the capsule endoscope 3, the images subjected to the processes are not limited to the images taken by the capsule endoscope 3. These embodiments can be used in the same manner for extracting a group of digest images from some other time-series images, such as video images or a series of continuous shooting still images.

The image processing device 10 according to the first embodiment and the image processing device 10b according to the second embodiment can be implemented by executing a predetermined computer program by a computer system, such as a personal computer or a work station. A computer system that has the same functions as in the image processing device 10 according to the first embodiment and the image processing device 10b according to the second embodiment and executes the image processing programs 141 and 141b is described below.

FIG. 16 is a schematic diagram of the configuration of a computer system 200 used in the embodiments. FIG. 17 is a block diagram of a main unit 210 included in the computer system 200. As shown in FIG. 16, the computer system 200 includes the main unit 210 and a display 220 that displays information, such as images, on a display screen 221 under an instruction received from the main unit 210. The computer system 200 further includes a keyboard 230 with which various information is input to the computer system 200 and a mouse 240 with which an arbitrary position on the display screen 221 of the display 220 is specified.

The main unit 210 included in the computer system 200, as shown in FIG. 17, includes a CPU 211, a RAM 212, a ROM 213, a hard disk drive (HDD) 214, a CD-ROM drive 215 that receives a CD-ROM 260, a USB port 216 that connects a USB memory 270 to the computer system 200 in a detachable manner, an I/O interface 217 that connects the display 220, the keyboard 230, and the mouse 240 to the computer system 200, and a LAN interface 218 that connects the computer system 200 to a local area network/wide area network (LAN/WAN) N1.

The computer system 200 is connected to a modem 250 that allows the computer system 200 to connect to a public line N3, such as the Internet, and is connected to external devices, such as a personal computer (PC) 281, a server 282, and a printer 283, via the LAN interface 218 and the LAN/WAN N1.

The computer system 200 reads the image processing program (e.g., the image processing program 141 according to the first embodiment and the image processing program 141b according to the second embodiment) from a predetermined recording medium and executes the read computer program, thereby implementing the image processing device. Not limited to the CD-ROM 260 and the USB memory 270, the predetermined recording medium is implemented by any types of recording mediums that stores therein the image processing program in the form readable by the computer system 200, such as "movable physical media" that include an MO disk, a DVD disk, a flexible disk (FD), a magnet-optical disk, and an IC card, "stationary physical media" that include built-in or external devices that are connected to the computer system 200, such as the HDD 214, the RAM 212, and the ROM 213, and "communication media" that are used as temporal memories of the computer program and include the public line N3 that is connected to the computer system 200 via the modem 250, the external computer system (PC) 281, the LAN/WAN N1 that is connected to the server 282, and etc.

The image processing program is stored in a recording medium that is a movable physical medium, a stationary physical medium, a communication medium, or the like in the form readable by the computer. The computer system 200 reads the image processing program from the recording medium and executes the read image processing program, thereby implementing the image processing device. The device that executes the image processing program is not limited to the computer system 200 and some other devices, such as the external computer system (PC) 281 or the server 282 can be configured to execute the image processing program. Moreover, it is allowable for two or more of these devices to execute the image processing program together.

According to the present invention, a group of primary digest images is extracted from time-series images by selecting the time-series images one by one and calculating the amount of change between the selected image and an image close to the selected image. The amount of change in each section of the time-series images defined by the primary digest images is then calculated. After that, a group of digest images is extracted from the time-series images using the calculated amounts of change between the images and the calculated amounts of change in sections. Therefore, a group of appropriate digest images is extracted from the time-series images in such a manner that both change between the individual images indicated by the amount of change between the images and change over the time-series images indicated by the amount of change in section are taken into consideration.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device for processing a plurality of time-series images taken at different points in time and arranged in chronological order, the image processing device comprising:
    a change-between-images calculating unit configured to:
        select images from the plurality of time-series images, wherein a selected image from the plurality of time-series images is a focus image, and
        calculate an amount-of-change-in-image for the focus image, wherein the amount-of-change-in-image indicates an amount of change between the focus image and a close image from the plurality of time-series images temporally close to the focus image;

a primary-digest-image extracting unit configured to extract a plurality of primary digest images from the plurality of time-series images based on the magnitude of the amount-of-change-in-image for each focus image in the plurality of time-series images;

a change-in-section calculating unit configured to:
select images from the plurality of primary digest images, wherein a selected image from the plurality of primary digest images is a focus primary digest image,
for the focus primary digest image, select an image from the plurality of time-series images as a late-section image, wherein the late-section image is a predetermined number of images earlier in chronological order than the focus primary digest image, and
calculate an amount-of-change-in-section for the late-section image, wherein the amount-of-change-in-section indicates an amount of change between the late-section image and a preceding primary digest image from the plurality of primary digest images, the preceding primary digest image being one image earlier in chronological order than the focus primary digest image; and a digest-image extracting unit configured to extract a plurality of digest images from:
the plurality of primary digest images, and
the plurality of late-section images corresponding to the plurality of focus primary digest images.

2. The image processing device according to claim 1, wherein the digest-image extracting unit comprises a first sorting unit configured to sort the plurality of primary digest images and the plurality of late section images by the magnitudes of the amount-of-change-in-image of the plurality of primary digest images and the magnitudes of the amount-of-change-in-section of the plurality of late section images, and
wherein the digest-image extracting unit is configured to extract a predetermined number of images as the plurality of digest images from the plurality of primary digest images and the plurality of late-section images in accordance with a result of the sorting performed by the first sorting unit, the predetermined number of images having largest magnitudes of change indicated by either the magnitudes of the amount-of-change-in-image of the plurality of primary digest images or the magnitudes of the amount-of-change-in-section of the plurality of late-section images.

3. The image processing device according to claim 1, wherein the digest-image extracting unit is configured to extract an image from the plurality of primary digest images having a magnitude of the amount-of-change-in-image that is greater than a predetermined threshold as a digest image and/or an image from the plurality of late-section images having a magnitude of the amount-of-change-in-section that is greater than or equal to the predetermined threshold as a digest image.

4. The image processing device according to claim 1 wherein the late-section image is later in chronological order than the preceding primary digest image.

5. The image processing device according to claim 1, wherein the primary-digest-image extracting unit comprises a second sorting unit configured to sort the plurality of time-series images by the magnitude of the amount-of-change-in-image for each focus image in the plurality of time-series images, and wherein the primary-digest-image extracting unit is configured to extract a predetermined number of images as the plurality of primary digest images from the plurality of time-series images in accordance with a result of the sorting performed by the second sorting unit, the predetermined number of images having largest magnitudes of the amount-of-change-in-image.

6. The image processing device according to claim 1, wherein the primary-digest image extracting unit is configured to extract an image from the plurality of time-series images having a magnitude of the amount-of-change-in-image that is greater than or equal to a predetermined threshold as a primary digest image.

7. A computer readable storage device having stored therein an image processing program including instructions for processing a plurality of time-series images taken at different points in time and arranged in chronological order, the instructions causing a computer to execute:
selecting images from the plurality of time-series images, wherein a selected image from the plurality of time-series images is a focus image;
calculating an amount-of-change-in-image for the focus image, wherein the amount-of-change-in-image indicates an amount of change between the focus image and a close image from the plurality of time-series images temporally close to the focus image;
extracting a plurality of primary digest images from the plurality of time-series images based on the magnitude of the amount-of-change-in-image for each focus image in the plurality of time-series images;
selecting images from the plurality of primary digest images, wherein a selected image from the plurality of primary digest images is a focus primary digest image;
for the focus primary digest image, selecting an image from the plurality of time-series images as a late-section image, wherein the late-section image is a predetermined number of images earlier in chronological order than the focus primary digest image;
calculating an amount-of-change-in-section for the late-section image, wherein the amount-of-change-in-section indicates an amount of change between the late-section image and a preceding primary digest image from the plurality of primary digest images, the preceding primary digest image being one image earlier in chronological order than the focus primary digest image; and
extracting a plurality of digest images from:
the plurality of primary digest images, and
the plurality of late-section images corresponding to the plurality of focus primary digest images.

8. An image processing method for processing a plurality of time-series images taken at different points in time and arranged in chronological order, the image processing method comprising:
selecting images from the plurality of time-series images, wherein a selected image from the plurality of time-series images is a focus image,
calculating an amount-of-change-in-image for the focus image, wherein the amount-of-change-in-image indicates an amount of change between the focus image and a close image from the plurality of time-series images temporally close to the focus image;
extracting a plurality of primary digest images from the plurality time-series images based on the magnitude of the amount-of-change-in-image for each focus image in the plurality of time-series images;

selecting images from the plurality of primary digest images, wherein a selected image from the plurality of primary digest images is a focus primary digest image;

for the focus primary digest image, selecting an image from the plurality of time-series images as a late-section image, wherein the late-section image is a predetermined number of images earlier in chronological order than the focus primary digest image;

calculating an amount-of-change-in-section for the late-section image, wherein the amount-of-change-in-section indicate an amount of change between the late-section image and a preceding primary digest image from the plurality of primary digest images, the preceding primary digest image being one image earlier in chronological order than the focus primary digest image; and extracting a plurality of digest images from:
- the plurality of primary digest images, and
- the plurality of late-section images corresponding to the plurality of focus primary digest images.

* * * * *